(12) United States Patent
Zehir et al.

(10) Patent No.: US 11,264,119 B2
(45) Date of Patent: Mar. 1, 2022

(54) GENERATING CONFIGURABLE TEXT STRINGS BASED ON RAW GENOMIC DATA

(71) Applicant: Memorial Sloan Kettering Cancer Center, New York, NY (US)

(72) Inventors: Ahmet Zehir, New York, NY (US); John Scott Ziegler, Hoboken, NJ (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 0 days.

(21) Appl. No.: 16/960,005

(22) PCT Filed: Jan. 9, 2019

(86) PCT No.: PCT/US2019/012913
§ 371 (c)(1),
(2) Date: Jul. 2, 2020

(87) PCT Pub. No.: WO2019/139994
PCT Pub. Date: Jul. 18, 2019

(65) Prior Publication Data
US 2020/0388352 A1 Dec. 10, 2020

Related U.S. Application Data

(60) Provisional application No. 62/615,743, filed on Jan. 10, 2018.

(51) Int. Cl.
*G16B 45/00* (2019.01)
*G16B 10/00* (2019.01)

(52) U.S. Cl.
CPC ............. *G16B 45/00* (2019.02); *G16B 10/00* (2019.02)

(58) Field of Classification Search
None
See application file for complete search history.

(56) References Cited

U.S. PATENT DOCUMENTS

| | | | | |
|---|---|---|---|---|
| 6,005,566 | A * | 12/1999 | Jones ....................... | G06F 9/451 715/788 |
| 9,798,855 | B2 | 10/2017 | Dowds et al. | |
| 2014/0274731 | A1 | 9/2014 | Raymond et al. | |
| 2014/0297196 | A1 | 10/2014 | Olson | |
| 2018/0211002 | A1 * | 7/2018 | Devogelaere .......... | G16B 30/00 |

FOREIGN PATENT DOCUMENTS

| | | |
|---|---|---|
| CN | 104871164 | 8/2015 |
| WO | WO-2016/043974 | 3/2016 |
| WO | WO-2016/139534 A2 | 9/2016 |
| WO | WO-2017/220508 A1 | 12/2017 |

OTHER PUBLICATIONS

Fan et al. The clinical utility of next-generation sequencing for identifying chromosome disease syndromes in human embryos Reproductive Biomedicine Online vol. 31, pp. 62-70 (Year: 2015).*
Li et al. SOAP2: an improved ultrafast tool for short read alignment Bioinformatics vol. 25, pp. 1966-1967 (Year: 2009).*
Pabinger et al. A survey of tools for variant analysis of next-generation genome sequencing data Briefings in Bioinformatics vol. 15, pp. 256-278 (Year: 2013).*
Zhang Overview of Sequence Data Formats Chapter 1, pp. 3-17 in Statistical Genomics: Methods in Molecular Biology Ewy Mathe and Sean Davis (eds) Springer Science+Business Media New York (Year: 2016).*
Hansen Variant Calling From Next Generation Sequence Data Chapter 11, pp. 209-224 in Statistical Genomics: Methods in Molecular Biology Ewy Mathe and Sean Davis (eds) Springer Science+Business Media New York (Year: 2016).*
Wikipedia "Delimiter-separated values" downloaded from the internet on Jun. 10, 2021 at https://en.wikipedia.org/wiki.Delimiter-separated_values (Year: 2021).*
Abyzov et al. Genome Research vol. 21, pp. 974-984 (Year: 2011).*
International Search Report and Written Opinion, PCT/US2019/012913, Memorial Sloan Kettering Cancer Center (Mar. 27, 2019).
Chang et al., "iopython Tutorial and Cookbook", Dec. 20, 2017 (Dec. 20, 2017), XP055836358, Retrieved from the Internet: URL:https://web.archive.org/web/20171220131641/http://biopython.org/DIST/docs/tutori al/Tutorial.html#htoc281 [retrieved on Aug. 31, 2021].

\* cited by examiner

*Primary Examiner* — John S Brusca
(74) *Attorney, Agent, or Firm* — Foley & Lardner LLP

(57) ABSTRACT

A genomic data translation system can be configured to process next-generation sequencing information. The system can receive an output file including raw genome data. The system can parse the output file to determine segments corresponding to individual chromosomes. The system can identify ranges of nucleotides and determine the first set of genes included in a human reference genome listing that fall within the ranges. The system can also maintain a gene list of genes, and determine a matched set of genes that are included in the gene list and the first set of genes. The system can generate a configurable text string including non-configurable regions and configurable regions. The configurable regions can be populated with text based on the raw genomic data, a set of translation rules, and a set of translation text strings.

23 Claims, 10 Drawing Sheets

Fig. 3 arr[hg19] 1p36.33p11.2(849,466-121,343,783)x1-2, 1p36.33p11.2(882,802-121,339,317)x2 hmz, 1q21.1q44(143,932,349-249,224,684)x2-3, 3p26.3q29(61,891-197,851,986)x1-2, 5p15.33q23.2(113,576-122,743,770)x2-3, 5q23.2(122,754,648-125,309,139)x1, 5q23.2q35.3(125,310,541-180,719,789)x2-3, 6p21.33p21.32(31,400,396-33,324,366)x1, 6q11.1q24.1(62,234,522-141,816,536)x1, 6q24.1q24.2(141,817,110-142,824,950)x0, 6q24.2q27(142,832,801-170,919,482)x1, 7p22.3q36.3(43,360-159,119,707)x3, 9p24.3q34.3(203,861-141,020,389)x1-2, 11p15.5q25(230,615-134,938,470)x1-2, 12p12.1q21.1(22,603,641-75,264,408)x3-4, 12p13.33p12.1(166,332-22,569,681)x2 hmz, 12p13.33p12.1(173,786-21,866,502)x1-2, 12q21.1q24.33(75,278,352-133,778,166)x2 hmz. 12q21.2q24.33(76,162, 131 -133, 777,902)x1-2, 16p13.3q24.3(85,880-90,155,062)x1-2, 17p11.2q25.3(19,143,975-81,041,938)x2-3, 17p13.3p11.2(280,253-18,922,212)x1, 19p13.3q13.43(260,911-58,956,888)x1-2, 20p13q13.33(61,568-62,915,555)x2-3, 21q11.2q22.3(15,006,457-48,097,372)x2-3, Xp22.33q28(168,546-155,233,731)x2, Yp11.31q11.223(2,650,140-24,485,636)x2, Yq11.223q11.23(24,493,072-28,451,874)x3

300

| | |
|---|---|
| 501 | 1p36.33p11.2(849,466-121,343,783)x1-2, 1p36.33p11.2(882,802-121,339,317)x2 hmz, 1q21.1q44(143,932,349-249,224,684)x2-3, |
| 503 | 3p26.3q29(61,891-197,851,986)x1-2, |
| 505 | 5p15.33q23.2(113,576-122,743,770)x2-3, 5q23.2(122,754,648-125,309,139)x1, 5q23.2q35.3(125,310,541-180,719,789)x2-3, |
| 506 | 6p21.33p21.32(31,400,396-33,324,366)x1, 6q11.1q24.1(62,234,522-141,816,536)x1, 6q24.1q24.2(141,817,110-142,824,950)x0, 6q24.2q27(142,832,801-170,919,482)x1, |
| 507 | 7p22.3q36.3(43,360-159,119,707)x3, |
| 509 | 9p24.3q34.3(203,861-141,020,389)x1-2, |
| 511 | 11p15.5q25(230,615-134,938,470)x1-2, |
| 512 | 12p12.1q21.1(22,603,641-75,264,408)x3-4, 12p13.33p12.1(166,332-22,569,681)x2 hmz, 12p13.33p12.1(173,786-21,866,502)x1-2, 12q21.1q24.33(75,278,352-133,778,166)x2 hmz. 12q21.2q24.33(76,162, 131 -133, 777, 902)x1-2, |
| 516 | 16p13.3q24.3(85,880-90,155,062)x1-2, |
| 517 | 17p11.2q25.3(19,143,975-81,041,938)x2-3, 17p13.3p11.2(280,253-18,922,212)x1, |
| 519 | 19p13.3q13.43(260,911-58,956,888)x1-2, |
| 520 | 20p13q13.33(61,568-62,915,555)x2-3, |
| 521 | 21q11.2q22.3(15,006,457-48,097,372)x2-3, |
| 522 | Xp22.33q28(168,546-155,233,731)x2, |
| 524 | Yp11.31q11.223(2,650,140-24,485,636)x2, Yq11.223q11.23(24,493,072-28,451,874)x3 |

Fig. 5

SNP-array analysis detected unbalanced genomic aberrations. Please see the description of major findings below:

Chromosome 1: loss of heterozygosity of 1p (with and without copy number loss), overlapping TNFRSF14 gene; minor clone with gain of 1q;
Chromosome 3: minor clone with loss of chromosome 3;
Chromosome 5: minor clone with gain in segments 5p15.33-q23.2 and 5q23.2-q35.3;
Chromosome 6: loss of 6q;
Chromosome 7: gain of chromosome 7;
Chromosome 9: minor clone with loss of chromosome 9;
Chromosome 11: minor clone with loss of chromosome 11;
Chromosome 12: loss of heterozygosity (with and without copy number loss) in segments 12p13.33-p12.1 and 12q21.1-q24.33; gain (~4 copies) in segment 12p12.1-q21.1;
Chromosome 16: minor clone with loss of chromosome 16;
Chromosome 17: loss in segment 17p13.3-p11.2 resulting in the hemizygous deletion of TP53 gene; minor clone with gain in segment 17p11.2-q25.3;
Chromosome 19: minor clone with loss of chromosome 19;
Chromosome 20: minor clone with gain of chromosome 20;
Chromosome 21: minor clone with gain of 21q;
Chromosome X: gain of chromosome X;
Chromosome Y: gain in segment Yp11.31-q11.223

Note: Copy number change segments that are less than 5Mb in size (if any) are not reported above. If copy number change segments less than 5Mb in size are detected and contain known cancer genes from the MSK-IMPACT 401-gene HEME panel, they are listed below, based on the genes involved; otherwise, they are not reported.

The following genes exhibit Hemizygous deletion (1 copy):
NOTCH4 (6p21.33-p21.32), DAXX (6p21.33-p21.32), LTB (6p21.33-p21.32)

Fig. 7

GENERATING CONFIGURABLE TEXT STRINGS BASED ON RAW GENOMIC DATA

CROSS-REFERENCE TO RELATED APPLICATIONS

This application is a National Stage Application of PCT/US2019/012913, filed Jan. 9, 2019, which claims the benefit of and priority to U.S. Provisional Patent Application No. 62/615,743, filed Jan. 10, 2018, the entire contents of which are incorporated herein by reference.

FIELD OF THE DISCLOSURE

The present disclosure is generally directed to transforming raw genomic data into a readable text output.

BACKGROUND OF THE DISCLOSURE

Genomic data processing can include graphically displaying genomic output received from a next-generation sequencer. The graphical representation can include displaying the read frequency of particular genetic alterations within a tested nucleic acid sequence. The graphical representation, however, does not provide additional valuable information available in raw genomic data generated by the next-generation sequencers.

BRIEF SUMMARY OF THE DISCLOSURE

In one aspect, the disclosure includes a system to process next-generation sequencing information. The system includes one or more processors, and one or more memory elements including instructions, which when executed, cause the one or more processors to execute a number of actions. The actions include to receive, via a user interface, an output file generated by a next-generation sequencer. The actions further include to determine at least one segment in the output file, the at least one segment including a chromosome number, cytoband information, a nucleotide range, and a set of copy numbers. The actions also include to determine a first set of genes within the nucleotide range, the first set of genes included in a human reference genome listing. The actions further include to determine a matched set of genes, the matched set of genes including at least one gene appearing in a gene list that matches a subset of the first set of genes. In some embodiments, the at least one gene appearing in the gene list is cancer-related. The actions also include to generate a configurable text string, the configurable text string including a non-configurable text region, a first configurable text region, a second configurable text region, and a third configurable text region. The actions also include to include a first text in the first configurable text region based on the chromosome number, a second text in the second configurable text region based on the set of copy numbers, and a third text in the third configurable text region based on the matched set of genes. The actions additionally include to provide the configurable text string to an output interface.

In another aspect, the disclosure includes a method to process next-generation sequencing information. The method includes receiving, at one or more processors, via a user interface, an output file generated by a next-generation sequencer. The method also includes determining, at the one or more processors, at least one segment in the output file, the at least one segment including a chromosome number, cytoband information, a nucleotide range, and a set of copy numbers. The method further includes determining, at the one or more processors, a first set of genes within the nucleotide range, the first set of genes included in a human reference genome listing. The method further includes determining, at the one or more processors, a matched set of genes, the matched set of genes including at least one gene appearing in a gene list that matches a subset of the first set of genes. The method additionally includes generating, at the one or more processors, a configurable text string, the configurable text string including a non-configurable text region, a first configurable text region, a second configurable text region, and a third configurable text region. The method further includes including a first text in the first configurable text region based on the chromosome number, including a second text in the second configurable text region based on the set of copy numbers, and including a third text in the third configurable text region based on the matched set of genes. The method also includes providing, by the one or more processors, the configurable text string to an output interface.

In yet another aspect, the disclosure relates to a computer readable storage medium storing processor-executable instructions, which when executed by at least one processor causes the at least one processor to execute a number of actions. The actions include to receive, via a user interface, an output file generated by a next-generation sequencer. The actions further include to determine at least one segment in the output file, the at least one segment including a chromosome number, cytoband information, a nucleotide range, and a set of copy numbers. The actions also include to determine a first set of genes within the nucleotide range, the first set of genes included in a human reference genome listing. The actions further include to determine a matched set of genes, the matched set of genes including at least one gene appearing in a gene list that matches a subset of the first set of genes. In some embodiments, the at least one gene appearing in the gene list is cancer-related. The actions also include to generate a configurable text string, the configurable text string including a non-configurable text region, a first configurable text region, a second configurable text region, and a third configurable text region. The actions also include to include a first text in the first configurable text region based on the chromosome number, a second text in the second configurable text region based on the set of copy numbers, and a third text in the third configurable text region based on the matched set of genes. The actions additionally include to provide the configurable text string to an output interface.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIG. 3 illustrates an example raw genomic data generated by a next-generation sequencer;

FIG. 5 illustrates various segments identified by a genomic data translation system from the raw genomic data shown in FIG. 3;

FIG. 7 shows an example translated output of a translation engine based on raw genomic data, translation rules, and a gene list.

DETAILED DESCRIPTION

For purposes of reading the description of the various embodiments below, the following descriptions of the sections of the specification and their respective contents may be helpful:

Section A describes a network environment and computing environment which may be useful for practicing embodiments described herein.

Section B describes embodiments of systems and methods for translating raw genomic data generated by a next-generation sequencer to human readable text strings.

A. Computing and Network Environment

Figure 1A:
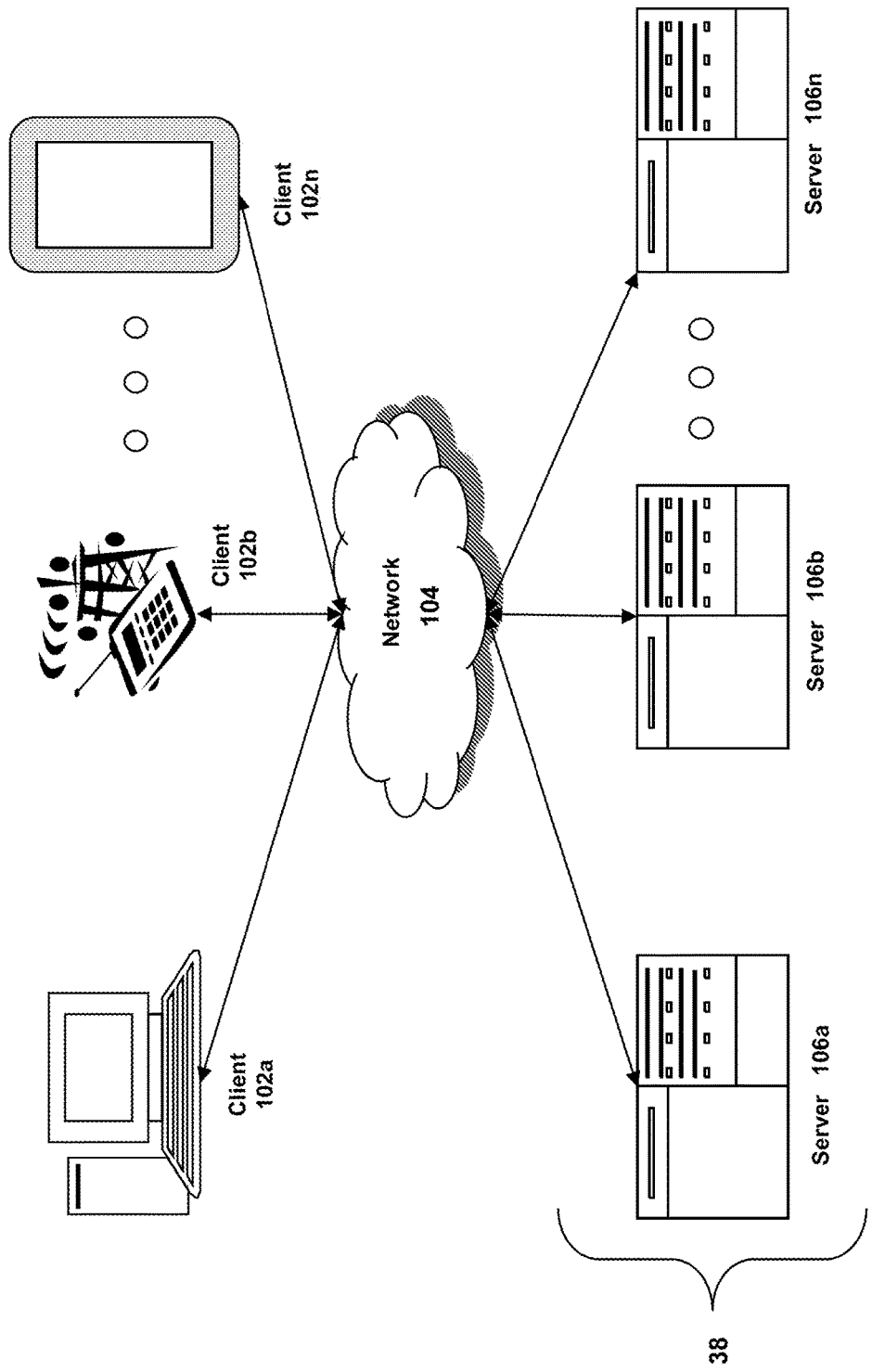
FIG. 1A is a block diagram depicting an embodiment of a network environment comprising a client device in communication with server device.

Prior to discussing specific embodiments of the present solution, it may be helpful to describe aspects of the operating environment as well as associated system components (e.g., hardware elements) in connection with the methods and systems described herein. Referring to FIG. 1A, an embodiment of a network environment is depicted. In brief overview, the network environment includes one or more clients 102a-102n (also generally referred to as local machine(s) 102, client(s) 102, client node(s) 102, client machine(s) 102, client computer(s) 102, client device(s) 102, endpoint(s) 102, or endpoint node(s) 102) in communication with one or more servers 106a-106n (also generally referred to as server(s) 106, node 106, or remote machine(s) 106) via one or more networks 104. In some embodiments, a client 102 has the capacity to function as both a client node seeking access to resources provided by a server and as a server providing access to hosted resources for other clients 102a-102n.

Although FIG. 1A shows a network 104 between the clients 102 and the servers 106, the clients 102 and the servers 106 may be on the same network 104. In some embodiments, there are multiple networks 104 between the clients 102 and the servers 106. In one of these embodiments, a network 104' (not shown) may be a private network and a network 104 may be a public network. In another of these embodiments, a network 104 may be a private network and a network 104' a public network. In still another of these embodiments, networks 104 and 104' may both be private networks.

The network 104 may be connected via wired or wireless links. Wired links may include Digital Subscriber Line (DSL), coaxial cable lines, or optical fiber lines. The wireless links may include BLUETOOTH, Wi-Fi, Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 104 may be any type and/or form of network. The geographical scope of the network 104 may vary widely and the network 104 can be a body area network (BAN), a personal area network (PAN), a local-area network (LAN), e.g. Intranet, a metropolitan area network (MAN), a wide area network (WAN), or the Internet. The topology of the network 104 may be of any form and may include, e.g., any of the following: point-to-point, bus, star, ring, mesh, or tree. The network 104 may be an overlay network which is virtual and sits on top of one or more layers of other networks 104'. The network 104 may be of any such network topology as known to those ordinarily skilled in the art capable of supporting the operations described herein. The network 104 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 104 may be a type of a broadcast network, a telecommunications network, a data communication network, or a computer network.

In some embodiments, the system may include multiple, logically-grouped servers 106. In one of these embodiments, the logical group of servers may be referred to as a server farm 38 or a machine farm 38. In another of these embodiments, the servers 106 may be geographically dispersed. In other embodiments, a machine farm 38 may be administered as a single entity. In still other embodiments, the machine farm 38 includes a plurality of machine farms 38. The servers 106 within each machine farm 38 can be heterogeneous—one or more of the servers 106 or machines 106 can operate according to one type of operating system platform (e.g., WINDOWS NT, manufactured by Microsoft Corp. of Redmond, Wash.), while one or more of the other servers 106 can operate on according to another type of operating system platform (e.g., Unix, Linux, or Mac OS X).

In one embodiment, servers 106 in the machine farm 38 may be stored in high-density rack systems, along with associated storage systems, and located in an enterprise data center. In this embodiment, consolidating the servers 106 in this way may improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 may be interconnected using a wide-area network (WAN) connection or a metropolitan-area network (MAN) connection. For example, a machine farm 38 may include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 may include one or more servers 106 operating according to a type of operating system, while one or more other servers 106 execute one or more types of hypervisors rather than operating systems. In these embodiments, hypervisors may be used to emulate virtual hardware, partition physical hardware, virtualize physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, Calif.; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 38 may be de-centralized. For example, one or more servers 106 may comprise components, subsystems and modules to support one or more management services for the machine farm 38. In one of these embodiments, one or more servers 106 provide functionality for management of dynamic data, including techniques for handling failover, data replication, and increasing the robustness of the machine farm 38. Each server 106 may communicate with a persistent store and, in some embodiments, with a dynamic store.

Server 106 may be a file server, application server, web server, proxy server, appliance, network appliance, gateway, gateway server, virtualization server, deployment server, SSL VPN server, or firewall. In one embodiment, the server 106 may be referred to as a remote machine or a node. In another embodiment, a plurality of nodes 290 may be in the path between any two communicating servers.

Figure 1B:
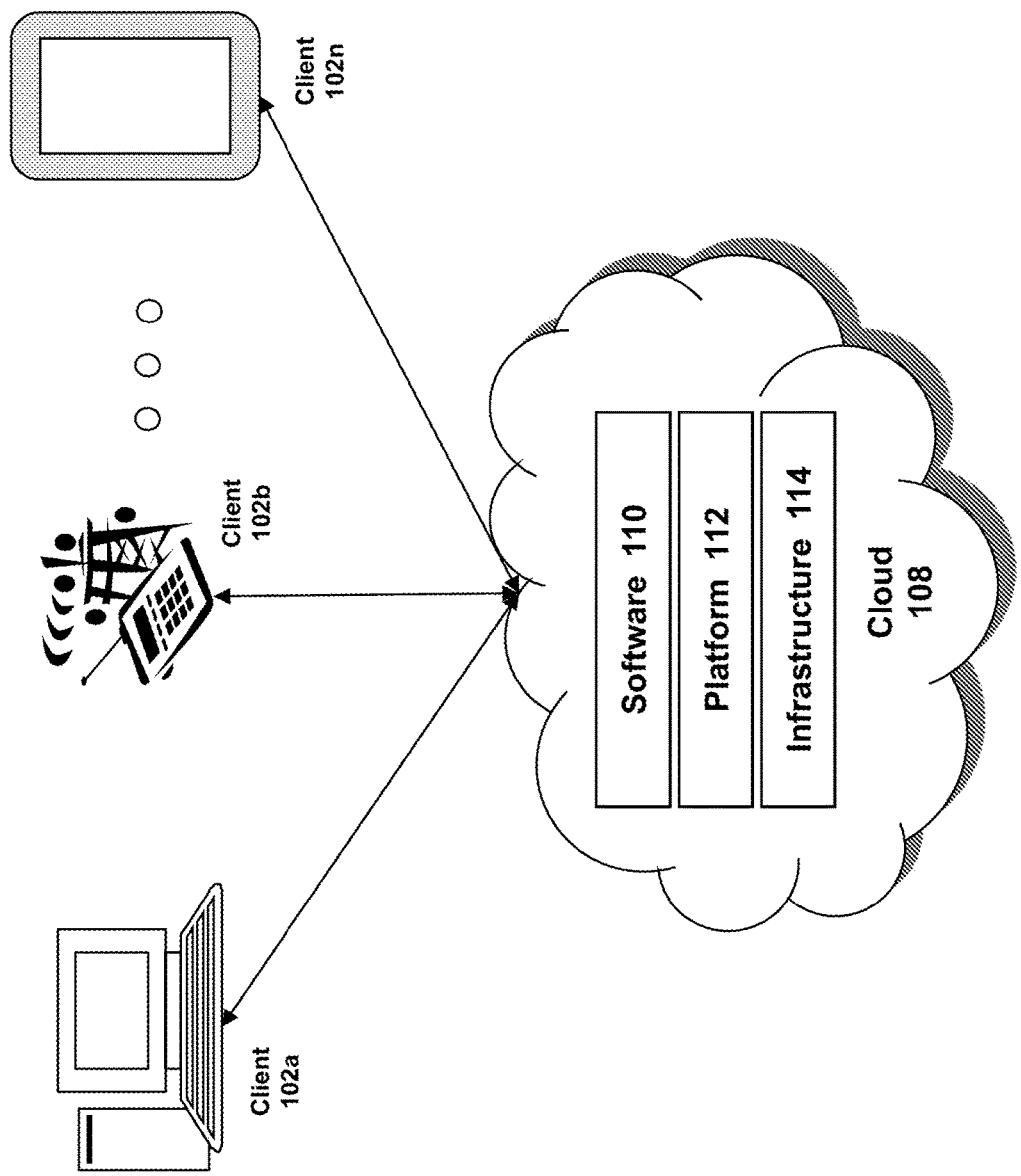
FIG. 1B is a block diagram depicting a cloud computing environment comprising client device in communication with cloud service providers.

Referring to FIG. 1B, a cloud computing environment is depicted. A cloud computing environment may provide client 102 with one or more resources provided by a network environment. The cloud computing environment may include one or more clients 102a-102n, in communication with the cloud 108 over one or more networks 104. Clients 102 may include, e.g., thick clients, thin clients, and zero clients. A thick client may provide at least some functionality even when disconnected from the cloud 108 or servers 106. A thin client or a zero client may depend on the connection to the cloud 108 or server 106 to provide functionality. A zero client may depend on the cloud 108 or other networks 104 or servers 106 to retrieve operating system data for the client device. The cloud 108 may include back end platforms, e.g., servers 106, storage, server farms or data centers.

The cloud 108 may be public, private, or hybrid. Public clouds may include public servers 106 that are maintained by third parties to the clients 102 or the owners of the clients. The servers 106 may be located off-site in remote geographical locations as disclosed above or otherwise. Public clouds may be connected to the servers 106 over a public network. Private clouds may include private servers 106 that are physically maintained by clients 102 or owners of clients. Private clouds may be connected to the servers 106 over a private network 104. Hybrid clouds 108 may include both the private and public networks 104 and servers 106.

The cloud 108 may also include a cloud based delivery, e.g. Software as a Service (SaaS) 110, Platform as a Service (PaaS) 112, and Infrastructure as a Service (IaaS) 114. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS can include infrastructure and services (e.g., EG-32) provided by OVH HOSTING of Montreal, Quebec, Canada, AMAZON WEB SERVICES provided by Amazon.com, Inc., of Seattle, Wash., RACKSPACE CLOUD provided by Rackspace US, Inc., of San Antonio, Tex., Google Compute Engine provided by Google Inc. of Mountain View, Calif., or RIGHTSCALE provided by RightScale, Inc., of Santa Barbara, Calif. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Wash., Google App Engine provided by Google Inc., and HEROKU provided by Heroku, Inc. of San Francisco, Calif. SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc., SALESFORCE provided by Salesforce.com Inc. of San Francisco, Calif., or OFFICE 365 provided by Microsoft Corporation. Examples of SaaS may also include data storage providers, e.g. DROPBOX provided by Dropbox, Inc. of San Francisco, Calif., Microsoft SKYDRIVE provided by Microsoft Corporation, Google Drive provided by Google Inc., or Apple ICLOUD provided by Apple Inc. of Cupertino, Calif.

Clients 102 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 102 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 102 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, Calif.). Clients 102 may also access SaaS resources through smartphone or tablet applications, including, e.g., Salesforce Sales Cloud, or Google Drive app. Clients 102 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 1C:
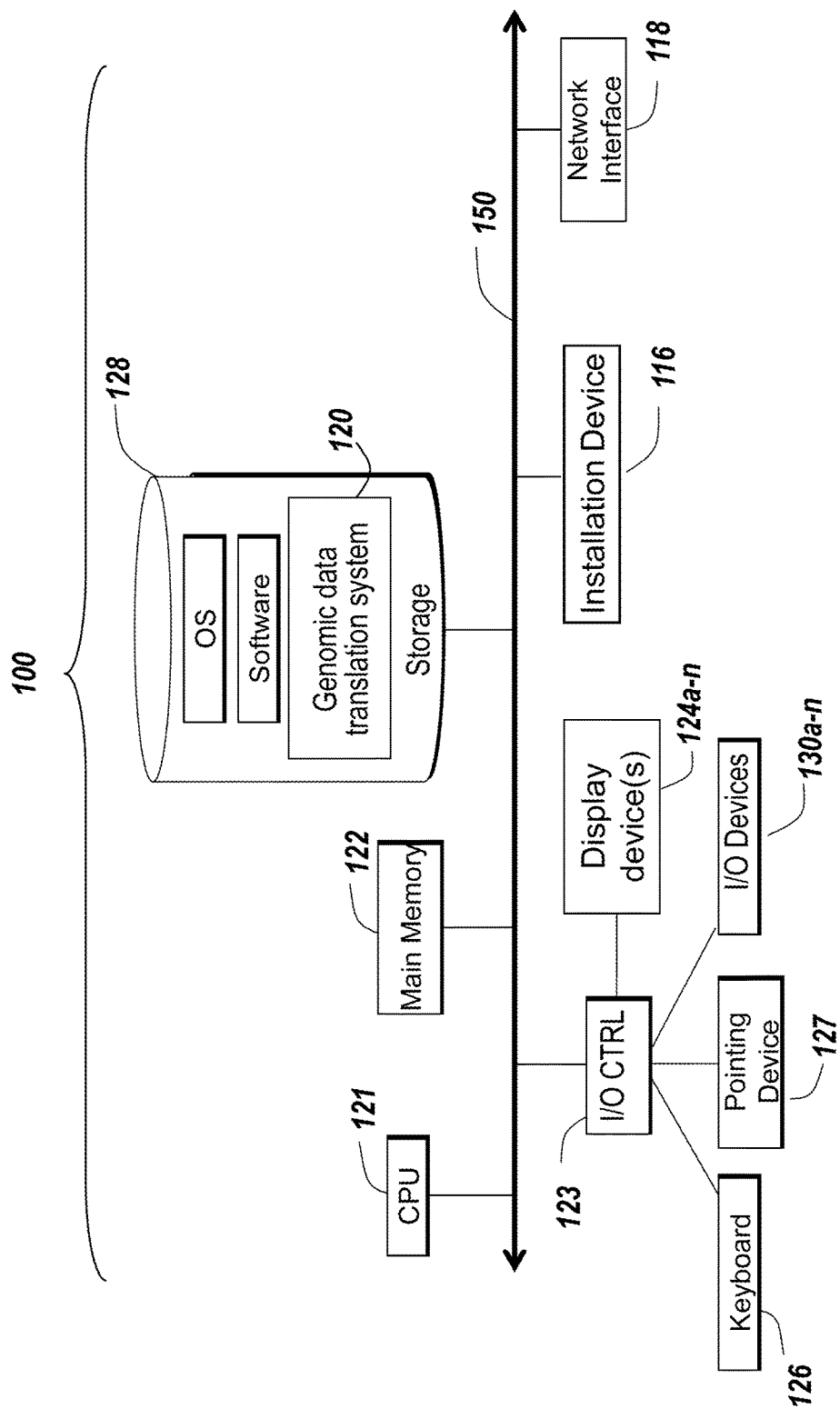
FIGS. 1C and 1D are block diagrams depicting embodiments of computing devices useful in connection with the methods and systems described herein.
Figure 1D:
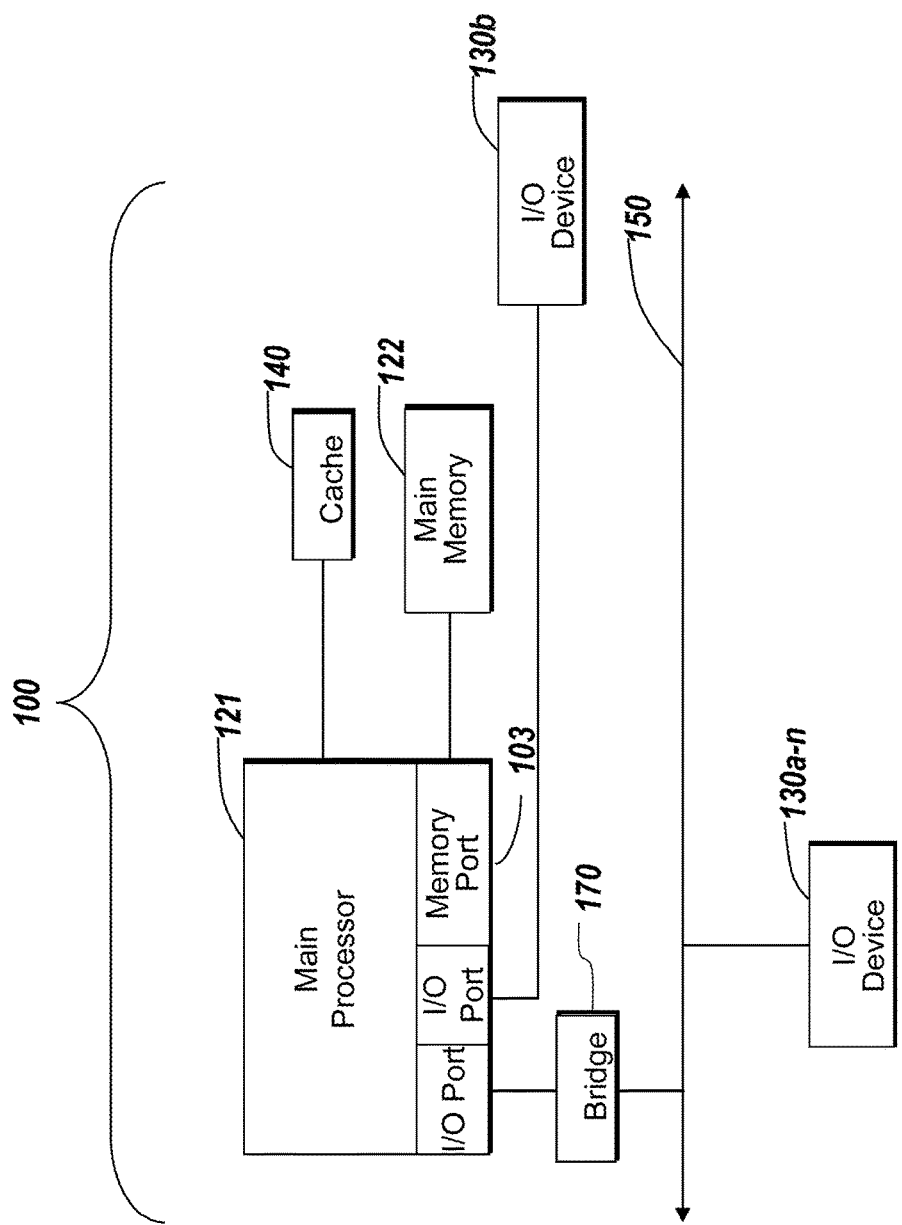

The client 102 and server 106 may be deployed as and/or executed on any type and form of computing device, e.g. a computer, network device or appliance capable of communicating on any type and form of network and performing the operations described herein. FIGS. 1C and 1D depict block diagrams of a computing device 100 useful for practicing an embodiment of the client 102 or a server 106. As shown in FIGS. 1C and 1D, each computing device 100 includes a central processing unit 121, and a main memory unit 122. As shown in FIG. 1C, a computing device 100 may include a storage device 128, an installation device 116, a network interface 118, an I/O controller 123, display devices 124a-124n, a keyboard 126 and a pointing device 127, e.g. a mouse. The storage device 128 may include, without limitation, an operating system, software, and a software of a genomic data translation system 120. As shown in FIG. 1D, each computing device 100 may also include additional optional elements, e.g. a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, e.g.: those manufactured by Intel Corporation of Mountain View, Calif.; those manufactured by Motorola Corporation of Schaumburg, Ill.; the ARM processor and TEGRA system on a chip (SoC) manufactured by Nvidia of Santa Clara, Calif.; the POWER7 processor, those manufactured by International Business Machines of White Plains, N.Y.; or those manufactured by Advanced Micro Devices of Sunnyvale, Calif. The computing device 100 may be based on any of these processors, or any other processor capable of operating as described herein. The central processing unit 121 may utilize instruction level parallelism, thread level parallelism, different levels of cache, and multi-core processors. A multi-core processor may include two or more processing units on a single computing component. Examples of multi-core processors include the AMD PHENOM IIX2, INTEL CORE i5 and INTEL CORE i7.

Main memory unit 122 may include one or more memory chips capable of storing data and allowing any storage location to be directly accessed by the microprocessor 121. Main memory unit 122 may be volatile and faster than storage 128 memory. Main memory units 122 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 122 or the storage 128 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 122 may be based on any of the above described memory chips, or any other available memory chips capable of operating as described herein. In the embodiment shown in FIG. 1C, the processor 121 communicates with main memory 122 via a system bus 150 (described in more detail below). FIG. 1D depicts an embodiment of a computing device 100 in which the processor communicates directly with main memory 122 via a memory port 103. For example, in FIG. 1D the main memory 122 may be DRDRAM.

FIG. 1D depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1D, the processor 121 communicates with various I/O devices 130 via a local system bus 150. Various buses may be used to connect the central processing unit 121 to any of the I/O devices 130, including a PCI bus, a PCI-X bus, or a PCI-Express bus, or a NuBus. For embodiments in which the I/O device is a video display 124, the processor 121 may use an Advanced Graphics Port (AGP) to communicate with the display 124 or the I/O controller 123 for the display 124. FIG. 1D depicts an embodiment of a computer 100 in which the main processor 121 communicates directly with I/O device 130b or other processors 121' via HYPERTRANSPORT, RAPIDIO, or INFINIBAND communications technology. FIG. 1D also depicts an embodiment in which local busses and direct communication are mixed: the processor 121 communicates with I/O device 130a using a local interconnect bus while communicating with I/O device 130b directly.

A wide variety of I/O devices 130a-130n may be present in the computing device 100. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 130a-130n may include a combination of multiple input or output devices, including, e.g., Microsoft KINECT, Nintendo Wiimote for the WII, Nintendo WII U GAMEPAD, or Apple IPHONE. Some devices 130a-130n allow gesture recognition inputs through combining some of the inputs and outputs. Some devices 130a-130n provides for facial recognition which may be utilized as an input for different purposes including authentication and other commands. Some devices 130a-130n provides for voice recognition and inputs, including, e.g., Microsoft KINECT, SIRI for IPHONE by Apple, Google Now or Google Voice Search.

Additional devices 130a-130n have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, may have larger surfaces, such as on a table-top or on a wall, and may also interact with other electronic devices. Some I/O devices 130a-130n, display devices 124a-124n or group of devices may be augment reality devices. The I/O devices may be controlled by an I/O controller 123 as shown in FIG. 1C. The I/O controller may control one or more I/O devices, such as, e.g., a keyboard 126 and a pointing device 127, e.g., a mouse or optical pen. Furthermore, an I/O device may also provide storage and/or an installation medium 116 for the computing device 100. In still other embodiments, the computing device 100 may provide USB connections (not shown) to receive handheld USB storage devices. In further embodiments, an I/O device 130 may be a bridge between the system bus 150 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 124a-124n may be connected to I/O controller 123. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopy. Display devices 124a-124n may also be a head-mounted display (HMD). In some embodiments, display devices 124a-124n or the corresponding I/O controllers 123 may be controlled through or have hardware support for OPENGL or DIRECTX API or other graphics libraries.

In some embodiments, the computing device 100 may include or connect to multiple display devices 124a-124n, which each may be of the same or different type and/or form. As such, any of the I/O devices 130a-130n and/or the I/O controller 123 may include any type and/or form of suitable hardware, software, or combination of hardware and software to support, enable or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In one embodiment, a video adapter may include multiple connectors to interface to multiple display devices 124a-124n. In other embodiments, the computing device 100 may include multiple video adapters, with each video adapter connected to one or more of the display devices 124a-124n. In some embodiments, any portion of the operating system of the computing device 100 may be configured for using multiple displays 124a-124n. In other embodiments, one or more of the display devices 124a-124n may be provided by one or more other computing devices 100a or 100b connected to the computing device 100, via the network 104. In some embodiments software may be designed and constructed to use another computer's display device as a second display device 124a for the computing device 100. For example, in one embodiment, an Apple iPad may connect to a computing device 100 and use the display of the device 100 as an additional display screen that may be used as an extended desktop. One ordinarily skilled in the art will recognize and appreciate the various ways and embodiments that a computing device 100 may be configured to have multiple display devices 124a-124n.

Referring again to FIG. 1C, the computing device 100 may comprise a storage device 128 (e.g. one or more hard disk drives or redundant arrays of independent disks) for storing an operating system or other related software, and for storing application software programs such as any program related to the software for the genomic data translation system 120. Examples of storage device 128 include, e.g., hard disk drive (HDD); optical drive including CD drive, DVD drive, or BLU-RAY drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 128 may be non-volatile, mutable, or read-only. Some storage device 128 may be internal and connect to the computing device 100 via a bus 150. Some storage devices 128 may be external and connect to the computing device 100 via an I/O device 130 that provides an external bus. Some storage device 128 may connect to the computing device 100 via the network interface 118 over a network 104, including, e.g., the Remote Disk for MACBOOK AIR by Apple. Some client devices 100 may not require a non-volatile storage device 128 and may be thin clients or zero clients 102. Some storage device 128 may also be used as an installation device 116, and may be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 100 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 102. An application distribution platform may include a repository of applications on a server 106 or a cloud 108, which the clients 102a-102n may access over a network 104. An application distribution platform may include application developed and provided by various developers. A user of a client device 102 may select, purchase and/or download an application via the application distribution platform.

Furthermore, the computing device 100 may include a network interface 118 to interface to the network 104 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 100 communicates with other computing devices 100' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Fla. The network interface 118 may comprise a built-in network adapter, network interface card, PCMCIA network card, EXPRESSCARD network card, card bus network adapter, wireless network adapter, USB network adapter, modem or any other device suitable for interfacing the computing device 100 to any type of network capable of communication and performing the operations described herein.

A computing device 100 of the sort depicted in FIGS. 1B and 1C may operate under the control of an operating system, which controls scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2022, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Wash.; MAC OS and iOS, manufactured by Apple, Inc. of Cupertino, Calif.; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, Calif., among others. Some operating systems, including, e.g., the CHROME OS by Google, may be used on zero clients or thin clients, including, e.g., CHROMEBOOKS.

The computer system 100 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 100 has sufficient processor power and memory capacity to perform the operations described herein. In some embodiments, the computing device 100 may have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 100 is a gaming system. For example, the computer system 100 may comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Wash.

In some embodiments, the computing device 100 is a digital audio player such as the Apple IPOD, IPOD Touch, and IPOD NANO lines of devices, manufactured by Apple Computer of Cupertino, Calif. Some digital audio players may have other functionality, including, e.g., a gaming system or any functionality made available by an application from a digital application distribution platform. For example, the IPOD Touch may access the Apple App Store. In some embodiments, the computing device 100 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 100 is a tablet e.g. the IPAD line of devices by Apple; GALAXY TAB family of devices by Samsung; or KINDLE FIRE, by Amazon.com, Inc. of Seattle, Wash. In other embodiments, the computing device 100 is an eBook reader, e.g. the KINDLE family of devices by Amazon.com, or NOOK family of devices by Barnes & Noble, Inc. of New York City, N.Y.

In some embodiments, the communications device 102 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc.; or a Motorola DROID family of smartphones. In yet another embodiment, the communications device 102 is a laptop or desktop computer equipped with a web browser and a microphone and speaker system, e.g. a telephony headset. In these embodiments, the communications devices 102 are web-enabled and can receive and initiate phone calls. In some embodiments, a laptop or desktop computer is also equipped with a webcam or other video capture device that enables video chat and video call.

In some embodiments, the status of one or more machines 102, 106 in the network 104 are monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

B. Processing of Raw Genomic Data

Figure 2:
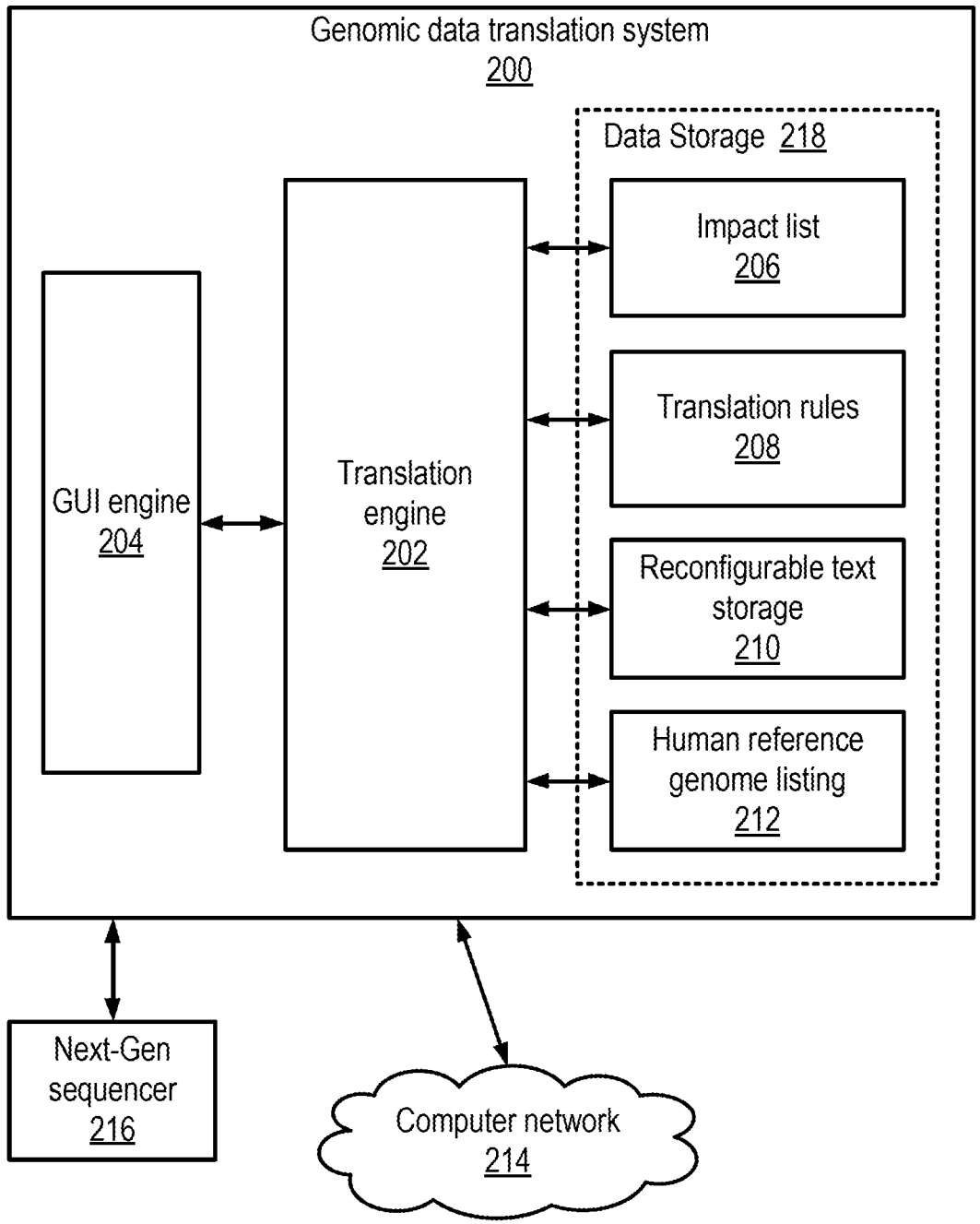
FIG. 2 illustrates a computer environment for translating raw genomic data generated by a next-generation sequencer to human readable text strings.

FIG. 2 illustrates a genomic data translation system 200, similar to the genomic data translation system 120 shown in FIG. 1C. As discussed below, the genomic data translation system 200 can receive raw genomic data (such as, for example, in a spread sheet or a comma-separated text file), and generate data indicating gene and chromosome level abnormalities identified in the raw genomic data. The genomic data translation system 200 includes a translation engine 202, a graphical user interface (GUI) engine 204, and a data storage 218. The data storage 218 can store a gene list 206, translation rules 208, reconfigurable text storage 210, and human reference genome listing 212. The GUI engine 204 can provide a GUI for display on a monitor or other display devices. The GUI engine 204 also can receive user input from one or more input devices, such as keyboards, mouse, touch-screen, gesture detector, or other input devices. The GUI engine 204 can provide an interactive interface to allow the user to provide input to control the operation of the genomic data translation system 200. The genomic data translation system 200 also can be coupled to a computer network 214, which can include one or more wired or wireless networks such as, for example, Ethernet, Internet, WiFi network, Bluetooth network, and the like. The genomic data translation system 200 can be implemented using the computing systems discussed above in relation to FIGS. 1A-1D.

The genomic data translation system 200 can receive data from a next-generation genomic sequencer ("NG sequencer") 216, such as, for example, an Illumina sequencer, an Ion Torrent sequencer, and a 454 pyro-sequencer. The NG sequencer 216 can provide detailed chromosome analysis, and can employ techniques such as array comparative genomic hybridization (CGH), microarray, oligo array, single nucleotide polymorphism (SNP) array, whole genome array (WGA), and the like. The NG sequencer 216 can provide raw genomic data to the genomic data translation system 200. In particular, the NG sequencer 216 can generate raw genomic data including cytoband information. In some implementations, the genomic data translation system 200 can provide, vie the GUI engine 204, the capability to upload the raw genomic data generated by the NG sequencer 216, instead of directly receiving the raw genomic data from the NG sequencer 216.

FIG. 3 illustrates an example raw genomic data 300 generated by a next-generation sequencer. In particular, the raw genomic data 300 can include cytoband information. The cytoband information can correspond to one or more chromosomes that exhibit abnormalities. As such, the raw genomic data 300 may include cytoband genomic information of only chromosomes exhibiting genetic alterations. The raw genomic data 30 also can include chromosome identification data, a nucleotide range, and copy numbers indicating the number of copies of the corresponding gene region(s) present within the nucleotide range of the chromosome.

Figure 4:
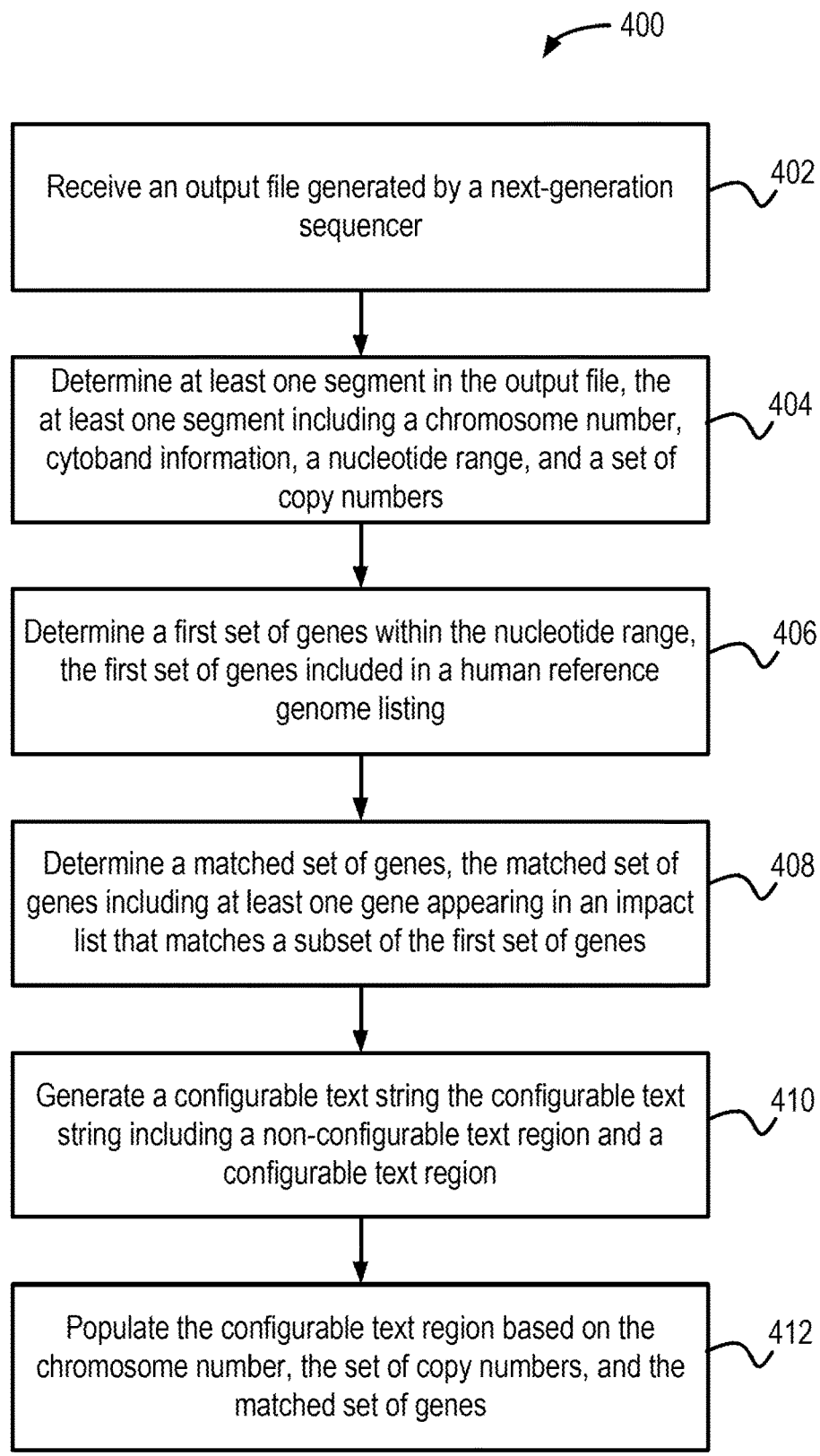
FIG. 4 shows a flow diagram of a process for translating raw genomic data.

FIG. 4 shows a flow diagram of a process 400 for translating raw genomic data. The process 400 can be used, for example, to translate raw genomic data 300 shown in FIG. 3. The process 400 can be executed by, for example, the genomic data translation system 200 shown in FIG. 2, and particularly the translation engine 202. The process 400 includes receiving an output file generated by a NG sequencer including raw genomic data (stage 402). Referring again to FIG. 2, the genomic data translation system 200 can receive the raw genomic data 300 from the NG sequencer 216 directly. For example, the genomic data translation system 200 can include one or more serial or parallel communication ports connected to the NG sequencer 216, and can receive the raw genomic data 300 from the NG sequencer 216 over the communication ports. In some implementations, the genomic data translation system 200 can receive a file, such as a data file, including the raw genomic data 300 from a user via the GUI engine 204.

The process 400 further includes determining at least one segment in the output file, the at least one segment including a chromosome number, cytoband information, a nucleotide range, and a set of copy numbers (stage 404). A segment can include genomic data associated with a chromosome. The raw genomic data 300 includes genomic data associated with several genes. The translation engine 202 can parse the raw genomic data 300 to identify the chromosomes for which genomic abnormality information is present in the raw genomic data. The translation engine 202 can determine the start of the file by searching for a start-of-file identifier, such as "arr[hg19]." This identifier can be unique to the NG sequencer 216 used, and may change based on the type of NG sequencer 216 used. In the raw genomic data 300 shown in FIG. 3, the identifier "arr[hg19]" indicates that the genomic analysis were done using an array technique (such as an array-CGH or SNP array) and is encoded using the 'Human Genome build-19'. Other builds such as "hg38," "hg18," "hg17," and the like may also be used for generating the raw genomic data 300. The translation engine 202 can parse the remainder of the raw genomic data 300, after the start-of-file identifier, to determine the start of a segment. For example, the translation engine 202 can search for an integer between 1 and 22 or the letters "X" and "Y" followed by the letters "p" or "q." The integers 1 to 22 correspond to the chromosome number, "X" and "Y" correspond to the X and Y chromosome, while "p" and "q" correspond to the short and long arm, respectively, of the chromosome. The translation engine can determine the end of the segment by searching for the copy information indicated by the letter "x" followed by one or more integers, such as for example, "x2" or "x1-2."

FIG. 5 illustrates various segments identified by the genomic data translation system 200 from the raw genomic data shown in FIG. 3. In particular, the translation engine 202 identifies 15 segments: a segment for chromosome 1 501, a segment for chromosome 3 503, a segment for chromosome 5 505, a segment for chromosome 6 506, a segment for chromosome 7 507, a segment for chromosome 9 509, a segment for chromosome 11 511, a segment for chromosome 12 512, a segment for chromosome 16 516, a segment for chromosome 17 517, a segment for chromosome 19 519, a segment for chromosome 20 520, a segment for chromosome 21 521, a segment for chromosome X 522, and a segment for chromosome Y 524.

Each segment includes a chromosome number, such as, for example, the first integer of the segment "1," which indicates the chromosome number. Each segment also includes cytoband information, such as, for example, "1p36.33p11.2," and "1q21.1q44" which identify the cytoband within the short and the long arm of the first chromosome. Each segment also includes a nucleotide range, such as, for example, "(849,466-121,343,783)," which indicates the range of base pairs that have an anomaly or abnormality compared to a reference genome build. Further, each segment also includes copy numbers, such as, for example, "x1" which indicates that the base pairs within the corresponding nucleotide range are observed only once, instead of twice as expected in a normal subject. Other copy numbers, such as "x1-2" indicate that the base pairs within the corresponding nucleotide range are observed either once or twice.

The process 400 also includes determining a first set of genes within the nucleotide range, where the first set of genes are included in a human reference genome. The translation engine 202 can look-up the human reference genome listing 212 to determine the genes that are present within each range of nucleotides. The human reference genome has several versions, or builds. The translation engine 202 can determine the version to look-up based on the identifier "arr[hg19]," which in the example shown in FIG. 3, refers to the "hg19" version of the human genome listing. The translation engine 202 can, for example, look-up the nucleotide ranges (849,466-121,343,783), (882,802-121, 339,317), and (143,932,349-249,224,684) appearing in the first segment 501 to the human reference genome listing 212. The human reference genome listing 212 can return a first set of genes that are present within each of these nucleotide ranges. In some implementations, the human reference genome listing 212 may be located remotely from the genomic data translation system 200, at a server and can be communicated with over the computer network 214. In some such implementations, the translation engine 202 can transmit the nucleotide ranges to the server, which can look up the nucleotide ranges in the human reference genome listing 212 and, in response, send to the translation engine 202 the first set of genes that are present within each of these nucleotide ranges.

The process 400 also includes determining a matched set of genes, the matched set of genes including at least one gene appearing in a gene list 206 that matches a subset of the first set of genes (stage 408). The gene list 206 includes identities of the genes of interest to clinicians. The gene list 206 can include genes related to certain diseases or abnormalities. For example, genes including but not limited to TNFRSF14, TP53, NOTCH4, DAXX, and LTB can be included in the gene list 206. The gene list 206 may also include genes such as tumor suppressor genes, oncogenes, cell-signaling proteins, adapter proteins, cell surface receptors, soluble and/or membrane bound ligands, enzymes (e.g., proteases), chaperone proteins, transcription factors, structural proteins, cytoskeletal proteins, proteins that regulate angiogenesis, cell division, cell adhesion, and cell cycle progression etc. The gene list 206 may also include cancer-related genes and/or non-cancer related genes. In some embodiments, the gene list 206 includes genes that impact the function of a specific organ including but not limited to lungs, skin, heart, liver, kidney, pancreas, intestine, brain, eyes, ears, nose, and the like. In some embodiments, the gene list 206 includes genes that impact the function of a specific cell type including but not limited to neurons, epithelial cells, endothelial cells, striated, smooth or cardiac muscle cells, renal cells, pancreatic cells, intestinal cells, ocular cells, blood cells, sensory cells, interstitial cells, germ cells, extracellular matrix cells, secretory epithelial cells, hormone secreting cells, glial cells, and the like. In some embodiments, the gene list 206 includes at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 150, at least 200, at least 250, at least 300, at least 350, at least 400, at least 450, or at least 500 genes.

As mentioned above, the firsts set of genes is determined using a nucleotide range and the human reference genome listing 212. The translation engine 202 can compare the gene list 206 with the first set of genes to determine whether any of the genes in the gene list 206 appear in the first set of genes. For example, the translation engine 202 can look-up each gene in the gene list 206 in the first set of genes, and if there is a match, the identity of the gene can be added to the matched set of genes. The presence of abnormalities in the first set of genes that correspond to genes from the gene list 206 include genetic markers of clinical relevance and may indicate the nature and/or prognosis of a disease state (e.g., cancer) in a patient based on the raw genomic output corresponding to a patient nucleic acid sample that has been sequenced using the NG sequencer 216. Genetic abnormalities include deletions, insertions, translocations, minor clones, copy number variations and the like.

Figure 6:
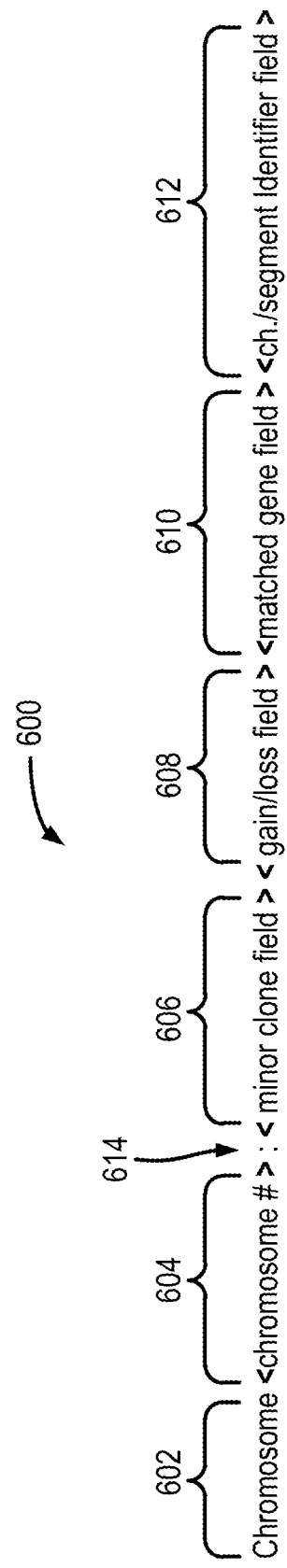
FIG. 6 shows an example configurable text string.

The process 400 additionally includes generating a configurable text string, the configurable text string including a non-configurable text region and a configurable text region (stage 410). FIG. 6 shows an example configurable text string 600. The configurable text string 600 includes a first non-configurable text region 602, a second non-configurable text region 614, and configurable text regions, namely, a chromosome #field 604, a minor clone field 606, a gain/loss field 608, a matched gene field 610, and a chromosome/ segment identifier field 612. The first non-configurable text region 602 includes the text "Chromosome," and the second non-configurable text region 614 includes the text ":". The first and the second non-configurable text regions 601 and 614 can remain unchanged by the data in the raw genomic data 300. However, the translation engine 202 can use other text instead of that shown in FIG. 6. The translation engine 202 can populate the configurable text regions based on the raw genomic data 300 and based on translation rules 208 (FIG. 2). The translation rules 208 can include one or more translation rules associated with each configurable region. The translation rules 208 for a configurable region provide the identity of the text to be entered in that configurable region based on the raw genomic data 300. The identity of the text can be included in the reconfigurable text storage 210, which can include a list of texts that can be inserted in each configurable region.

The process further includes populating the configurable text region based on the chromosome number, the set of copy numbers, and the matched set of genes (stage 412). FIG. 7 shows an example translated output 700 of the translation engine 202 based on the data in raw genomic data 300, translation rules 208, and the gene list 206. In particular, the translated output 700 includes a configurable text string corresponding to each chromosome identified in the raw genomic data 300, or corresponding to each segment identified in FIG. 5.

The chromosome #field 604 can be populated with the text corresponding to the chromosome number, such as, for example, "1", "6", etc. The translation rule for the chromosome #field can specify including the text of the number corresponding to the chromosome number of the segment. As shown in FIG. 7, the translated output 700 includes appropriate numbers in the chromosome #field for each chromosome.

The minor clone field 606 can be populated with the text "minor clone with" or no text at all, based on the absence of either a "p" or a "q" arm in the chromosome. For example, referring to the segment for the ninth chromosome 509 shown in FIG. 5, the long arm "q" is missing. As a result, the translation engine 202 may include the text "minor clone with" in the minor clone field, as shown in the configurable text string corresponding to chromosome 9 in the translated output 700.

The gain/loss field 608 can be populated with the texts "loss of" or "gain of" of no text at all based on the copy number. For example, the translation rule for the gain/loss field 608 can specify that if the copy number is less than 2, then the gain/loss field can be populated with the text "loss of," on the other hand, if the copy number is greater than 2, then the gain/loss field can be populated with the text "gain of." For example, referring to the segment for the ninth chromosome 509 shown in FIG. 5, the copy number is "1-2" which is less than 2. Therefore, the gain/loss field 608 can be populated with the text "loss of."

The matched gene field 610 can be populated with the text corresponding to a matched gene. For example, referring to the first segment 501 for the first chromosome shown in FIG. 5, the matched list includes the gene "TNFRSF14." Further, the segment including "hmz" which indicates loss of heterozygosity, is associated with the "p" arm. Therefore, the matched gene field 610 can be populated with the text "heterozygosity of 1p overlapping TNFRSF14 gene." The translated output 700 shown in FIG. 7 illustrates several examples of the text inserted in the matched gene field 610, two of which include the texts corresponding to chromosome 1 and chromosome 17.

The chromosome/segment identifier field 612 identifies the chromosome, segment, or cytoband that exhibits a gain or loss. This field can be populated with one of the chromosome number, the long/short arm identifier, or the cytoband identifier. For example, referring again to the segment for the ninth chromosome 509 shown in FIG. 5, the copy number is less than 2, therefore, the chromosome/segment identifier field 612 is populated with the text "chromosome 9," as shown in FIG. 7. In another example, the segment corresponding to chromosome 6 506 in FIG. 5 shows a copy number "x0," indicating a complete loss of the "q" arm. Therefore, the chromosome/segment identifier field 612 corresponding to the chromosome 6 can be populated with "6q," as shown in the translated output 700 in FIG. 7.

It is understood that the translation engine 202 is not limited to generating the number and types of configurable and non-configurable fields shown in FIGS. 6 and 7, and that additional configurable fields, or fewer configurable fields may also be used.

In some implementations, the translation engine 202 may determine content of the configurable text based on the number of base pairs in the nucleotide ranges of the chromosomes. For example, if the number of base pairs in a nucleotide range is less than 5 $10^6$ bases pairs (Mb), then the translation engine may forego providing the translated output in the form shown in the first portion 702, and instead may provide the translated output in the manner shown in the second portion 704. In the second portion 704, the translation engine 202 can provide a list of the genes that in the matched list and their corresponding segment.

What is claimed is:

1. A system comprising:
one or more processors; and
one or more memory elements including instructions, which when executed, cause the one or more processors to:
receive a computer file comprising a continuous text string having a plurality of textual segments based on copy number analysis of a patient sample using a human reference genome build, each textual segment comprising a chromosome number, cytoband information, a copy number parameter, nucleotide position termini associated with the copy number parameter, the nucleotide position termini defining a nucleotide range;
parse the continuous text string in the computer file to identify, for each textual segment, the chromosome number, cytoband information, the copy number parameter, and the nucleotide position termini associated with the copy number parameter, wherein parsing the continuous text string comprises locating, for each textual segment, (i) a textual segment start position by identifying the chromosome number, and (ii) a textual segment end position by identifying the copy number parameter;
for each textual segment, compare a set of genes within the nucleotide range to a corresponding genetic region in the human reference genome build to identify one or more disease-related genes that fall within the nucleotide range;
for each textual segment, translate, based on a plurality of translation rules,
(i) the chromosome number to a first text corresponding to the chromosome number,
(ii) the copy number parameter to a second text indicating whether a minor clone is present,
(iii) the copy number parameter and the nucleotide range into a third text indicating a gain or loss of the genetic region corresponding to the nucleotide range, and
(iv) the one or more disease-related genes that fall within the nucleotide range to a fourth text indicating a copy number feature; and
present, on a display screen, for at least one chromosome, a visual representation incorporating at least two of the following:
(i) a first text region populated with the first text corresponding to the chromosome number,
(ii) a second text region populated with the second text indicating whether the minor clone is present,
(iii) a third text region populated with the third text indicating the gain or loss of the genetic region corresponding to the nucleotide range, and
(iv) a fourth text region populated with the fourth text indicating the copy number feature.

2. The system of claim 1, wherein each identified textual segment corresponds to at least one of a short arm (p), a long arm (q), or a combination of the short arm and long arm of a chromosome identified by the chromosome number.

3. The system of claim 1, wherein the one or more memory elements include instructions, which when executed, cause the one or more processors to:
populate the third text region based on the copy number parameter and a gene loss-gain rule of the plurality of translation rules, the gene loss-gain rule specifying the third text to be "loss" when the copy number parameter includes a number less than 2.

4. The system of claim 1, wherein the human reference genome build includes at least one of GRCh38, GRCh37, NCBI Build 36.1, NCBI Build 35, NCBI Build 34, hg38, hg19, hg18, hg17, and hg16.

5. The system of claim 1, wherein the one or more disease-related genes includes at least one cancer related gene.

6. A method comprising:
receiving, by a genomic data translation computing system comprising one or more processors, a computer file comprising a continuous text string having a plurality of textual segments based on copy number analysis of a patient sample using a human reference genome build, each textual segment comprising a chromosome number, cytoband information, a copy number parameter, nucleotide position termini associated with the copy number parameter, the nucleotide position termini defining a nucleotide range;
parsing, by the genomic data translation computing system, the continuous text string in the computer file to identify, for each textual segment, the chromosome number, cytoband information, the copy number parameter, and the nucleotide position termini associated with the copy number parameter, wherein parsing the continuous text string comprises locating, for each textual segment, (i) a textual segment start position by identifying the chromosome number, and (ii) a textual segment end position by identifying the copy number parameter;

for each textual segment, comparing, by the genomic data translation computing system, a set of genes within the nucleotide range to a corresponding genetic region in the human reference genome build to identify one or more disease-related genes that fall within the nucleotide range;

for each textual segment, translating, by the genomic data translation computing system, based on a plurality of translation rules,
(i) the chromosome number to a first text corresponding to the chromosome number,
(ii) the copy number parameter to a second text indicating whether a minor clone is present,
(iii) the copy number parameter and the nucleotide range into a third text indicating a gain or loss of the genetic region corresponding to the nucleotide range, and (iv) the one or more disease-related genes that fall within the nucleotide range to a fourth text indicating a copy number feature;

presenting, by the genomic data translation computing system, on a display screen, for at least one chromosome, a visual representation incorporating at least two of the following:
(i) a first text region populated with the first text corresponding to the chromosome number,
(ii) a second text region populated with the second text indicating whether the minor clone is present,
(iii) a third text region populated with the third text indicating the gain or loss of the genetic region corresponding to the nucleotide range, and
(iv) a fourth text region populated with the fourth text indicating the copy number feature.

7. The method of claim 6, wherein each textual segment corresponds to at least one of a short arm (p), a long arm (q), or a combination of the short arm and long arm of a chromosome identified by the chromosome number.

8. The method of claim 6, wherein populating the third text region based on the copy number parameter and a gene loss-gain rule of the plurality of translation rules, the gene loss-gain rule specifying the third text to be "loss" when the copy number parameter includes a number less than 2.

9. The method of claim 6, wherein the human reference genome build includes at least one of GRCh38, GRCh37, NCBI Build 36.1, NCBI Build 35, NCBI Build 34, hg38, hg19, hg18, hg17, and hg16.

10. The method of claim 6, wherein the one or more disease-related genes includes at least one cancer related gene.

11. A computer readable storage medium storing processor-executable instructions, which when executed by at least one processor causes the at least one processor to:
receive, a computer file comprising a continuous text string having a plurality of textual segments based on copy number analysis of a patient sample using a human reference genome build, each textual segment comprising a chromosome number, cytoband information, a copy number parameter, nucleotide position termini associated with the copy number parameter, the nucleotide position termini defining a nucleotide range;
parse the text string in the computer file to identify, for each textual segment the chromosome number, cytoband information, the copy number parameter, and the nucleotide position termini associated with the copy number parameter, wherein parsing the text string comprises locating, for each textual segment (i) a textual segment start position by identifying the chromosome number, and (ii) a textual segment end position by identifying the copy number parameter;

for each textual segment, compare a set of genes within the nucleotide range to a corresponding genetic region in the human reference genome build to identify one or more disease-related genes that fall within the nucleotide range;

for each textual segment, translate, based on a plurality of translation rules,
(i) the chromosome number to a first text corresponding to the chromosome number,
(ii) the copy number parameter to a second text indicating whether a minor clone is present,
(iii) the copy number parameter and the nucleotide range and into a third text indicating a gain or loss of a genetic region corresponding to the nucleotide range, and
(iv) the one or more disease-related genes that fall within the nucleotide range to a fourth text indicating a copy number feature; and present, on a display screen, for at least one chromosome, a visual representation incorporating at least two of the following:
(i) a first text region populated with the first text corresponding to the chromosome number,
(ii) a second text region populated with the second text indicating whether the minor clone is present,
(iii) a third text region populated with the third text indicating the gain or loss of the genetic region corresponding to the nucleotide range, and
(iv) a fourth text region populated with the fourth text indicating the copy number feature.

12. The computer readable storage medium of claim 11, wherein each of the textual segment corresponds to at least one of a short arm (p), a long arm (q), or a combination of the short arm and long arm of a chromosome identified by the chromosome number.

13. The computer readable storage medium of claim 11, further comprising instructions, which when executed by the at least one processor causes the at least one processor to:
populate the third text region based on the copy number and a gene loss-gain rule of the plurality of translation rules stored in memory, the gene loss-gain rule specifying the second text to be "loss" when the copy number parameter includes a number less than 2.

14. The computer readable storage medium of claim 11, wherein the human reference genome build includes at least one of GRCh38, GRCh37, NCBI Build 36.1, NCBI Build 35, NCBI Build 34, hg38, hg19, hg18, hg17, and hg16.

15. The system of claim 1, wherein the copy number feature indicates that the gene of the plurality of genes is heterozygous.

16. The system of claim 1, wherein the one or more memory elements include instructions, which when executed, cause the one or more processors to present, in the visual representation, for the at least one chromosome, based on the nucleotide range, a fifth text region indicating at least one of a short arm (p), a long arm (q), or a combination of the short arm and long arm of a chromosome identified by the chromosome number.

17. The method of claim 6, wherein the copy number feature indicates that the gene of the plurality of genes is heterozygous.

18. The method of claim 6, further comprising presenting, by the genomic data translation computing system, in the visual representation, for the at least one chromosome, based on the nucleotide range, a fifth text region identifying at least one of a short arm (p), a long arm (q), or a combination of the short arm and long arm of a chromosome identified by the chromosome number.

19. The computer readable storage medium of claim 11, wherein the copy number feature indicates that the gene of the plurality of genes is heterozygous.

20. The computer readable storage medium of claim 11, further comprising instructions, which when executed by the at least one processor causes the at least one processor to present, in the visual representation, for the at least one chromosome, based on the nucleotide range, a fifth text region identifying at least one of a short arm (p), a long arm (q), or a combination of the short arm and long arm of a chromosome identified by the chromosome number.

21. The system of claim 1, wherein the one or more disease-related genes are selected from the group consisting of tumor suppressor genes, oncogenes, cell-signaling proteins, adapter proteins, cell surface receptors, soluble and/or membrane bound ligands, enzymes, chaperone proteins, transcription factors, structural proteins, cytoskeletal proteins, and proteins that regulate cell division, and cell cycle progression.

22. The method of claim 6, wherein the one or more disease-related genes are selected from the group consisting of tumor suppressor genes, oncogenes, cell-signaling proteins, adapter proteins, cell surface receptors, soluble and/or membrane bound ligands, enzymes, chaperone proteins, transcription factors, structural proteins, cytoskeletal proteins, and proteins that regulate cell division, and cell cycle progression.

23. The computer readable storage medium of claim 11, wherein the one or more disease-related genes are selected from the group consisting of tumor suppressor genes, oncogenes, cell-signaling proteins, adapter proteins, cell surface receptors, soluble and/or membrane bound ligands, enzymes, chaperone proteins, transcription factors, structural proteins, cytoskeletal proteins, and proteins that regulate cell division, and cell cycle progression.

* * * * *